United States Patent [19]

Shook

[11] Patent Number: 4,604,094

[45] Date of Patent: Aug. 5, 1986

[54] TOPOSCOPIC CATHETER AND METHOD OF FABRICATION

[75] Inventor: Daniel R. Shook, Gaithersburg, Md.

[73] Assignee: The United States of America as represented by the Secretary of the Department of Health and Human Services, Washington, D.C.

[21] Appl. No.: 647,728

[22] Filed: Sep. 6, 1984

[51] Int. Cl.$^4$ .............................................. A61M 25/00
[52] U.S. Cl. ................... 604/271; 128/348.1
[58] Field of Search ................ 604/270–273, 604/93, 52, 53; 128/344, 348.1, 325

[56] References Cited

U.S. PATENT DOCUMENTS

| | | | |
|---|---|---|---|
| 805,851 | 11/1905 | Goldfarb | 604/271 |
| 3,459,175 | 8/1969 | Miller | 128/654 |
| 3,506,011 | 4/1970 | Silverman | 128/348 |
| 3,707,146 | 12/1972 | Cook et al. | 128/2 R |
| 4,043,345 | 8/1977 | Kramann et al. | 128/349 R |
| 4,077,610 | 3/1978 | Masuda | 254/134.4 |
| 4,243,040 | 1/1981 | Beecher | 604/271 X |
| 4,311,137 | 1/1982 | Gerard | 128/214.4 |
| 4,321,915 | 3/1982 | Leighton et al. | 128/4 |
| 4,365,635 | 12/1982 | Bowman | 128/675 |
| 4,437,857 | 3/1984 | Goldstein et al. | 604/271 |

*Primary Examiner*—Stephen C. Pellegrino
*Attorney, Agent, or Firm*—Holman & Stern

[57] ABSTRACT

An everting catheter assembly includes a primary catheter tube inside which an everting or toposcopic element is secured spaced from the distal end of the primary catheter tube and with the open head end of the toposcopic element facing away from the open distal end of the primary catheter. The bonding of the toposcopic element to the interior of the primary catheter is effected with the use of a hollow mandrel through which the toposcopic element extends so that a short length of the toposcopic element projects out from the mandrel and is folded back over a length of the outer surface of the mandrel at the mandrel forward end. The mandrel is withdrawn into the primary catheter tube to the desired location for bonding at which point a bond is effected by means of heat conducted to the mating surfaces through the catheter wall or deposited locally by a radiative technique and heating between the mating surfaces. The tail end of the everting catheter is secured to a seal tube of greater rigidity by disposing the open tail end of the toposcopic element over a bias-cut end of the seal tube. Bonding is effected by application of heat to the mating surfaces. The bias-cut on the seal tube permits complete collapse of the toposcopic element upon pressurization of the annular cylindrical region from which the eversion is effected. Since the protruding bias-cut does not preferentially bend so as to evert within itself, a geometrically unbalanced collapse of the toposcopic element occurs. Introduction of pressurized sterile eversion fluid media into the annular region is facilitated by means of a bleed tube extending to the lead end of the annular region so as to permit pre-existing gas to be bled from the annular region during pressurization.

34 Claims, 9 Drawing Figures

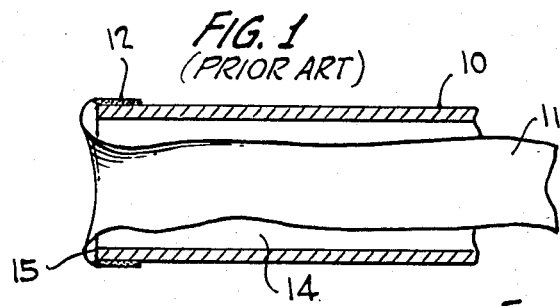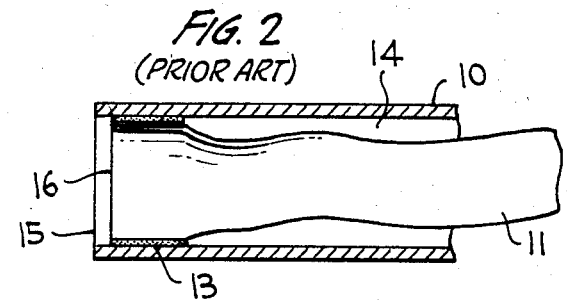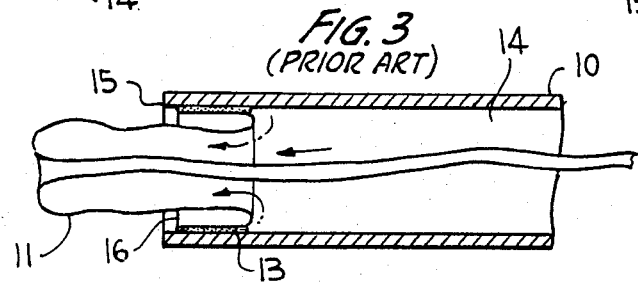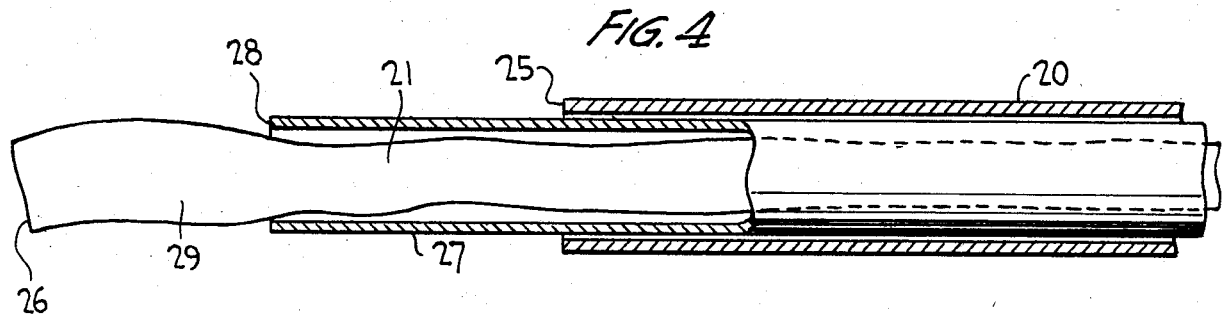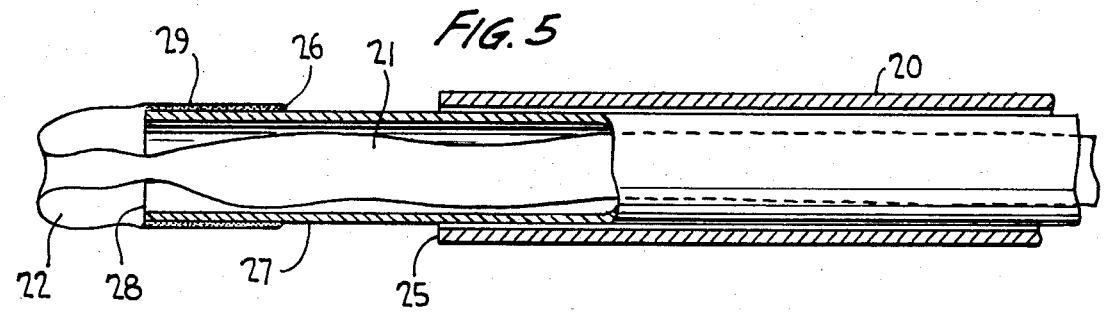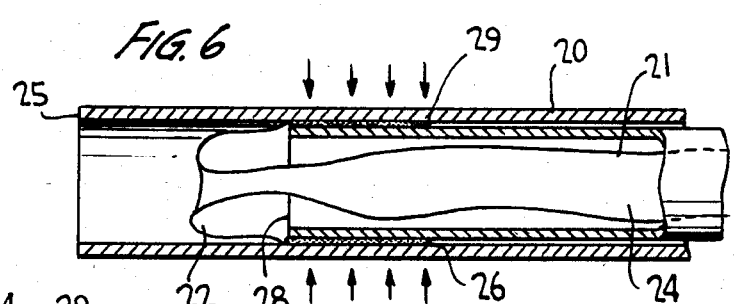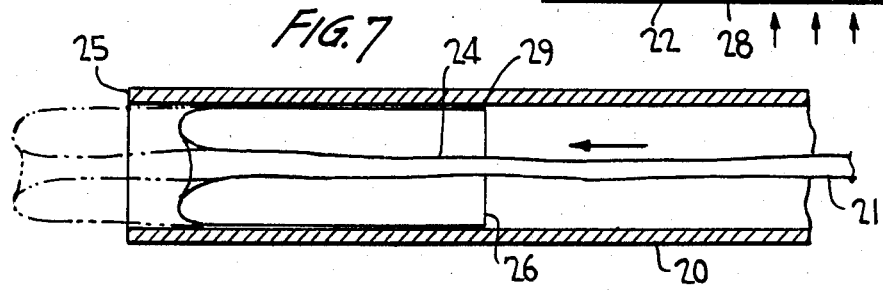

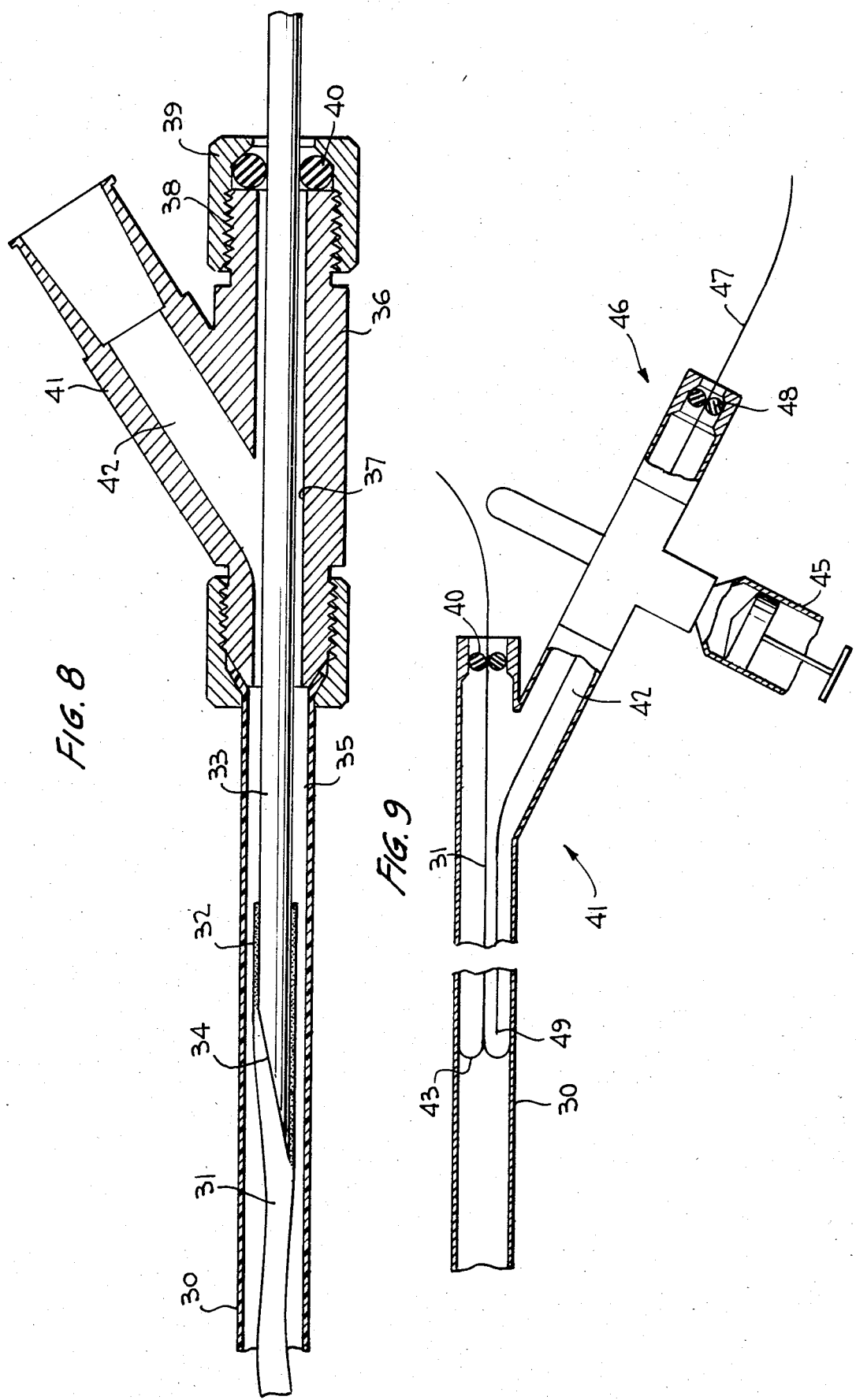

TOPOSCOPIC CATHETER AND METHOD OF FABRICATION

BACKGROUND OF THE INVENTION

1. Technical Field

The present invention relates to toposcopic or everting catheters and methods of fabrication of such catheters. The present invention is an improvement of the catheters and fabrication techniques described in U.S. patent application Ser. No. 06/022,219, now U.S. Pat. No. 4,437,857, filed Mar. 19, 1979 by Seth Goldstein and Robert Jones, and entitled "Method and Apparatus For Traversing Blood Vessels". The subject matter of that prior application is expressly incorporated herein, in its entirety, by this reference.

2. Discussion Of The Prior Art

A prior art everting catheter tube assembly is illustrated in FIG. 1 wherein a primary catheter tube 10 has a highly flexible thin-walled everting catheter tube 11 secured thereto. More specifically, the head or forward end of the everting catheter tube 11 is folded over the open distal end of primary catheter tube 10 and a short length 12 of the everting catheter tube is sealed upon or bonded to the outer circumference of the primary catheter tube. The annular space 14 between the exterior surface of everting catheter tube 11 and the interior surface of primary catheter tube 10 may be supplied with pressurized fluid to force eversion of the catheter tube out through the distal end 15 of the primary catheter tube 10. The everting catheter tube 11, when so everted, effectively rolls along the interior walls of a blood vessel or other anatomical passage.

Another prior art everting catheter assembly is illustrated in FIG. 2 wherein a short length 13 at the head end of everting catheter tube 11 is secured to the interior surface of primary catheter tube 10. The open head end 16 of everting catheter tube 11 faces in the same direction as the open distal end of primary catheter tube 10. As illustrated in FIG. 3, when pressurized fluid is applied to the annular space between the everting catheter tube 11 and the primary catheter tube 10, tube 11 advances as a function of the applied pressure, causing the inner tube to turn inside out upon itself (or evert) and unroll beyond the bond position 13 through the open end 15 of the primary catheter tube.

In both prior art embodiments the opposite end of the inner or everting tube 11 (i.e., the tail end, not illustrated in FIGS. 1-3), being unattached to the primary catheter tube, is dragged forward within the primary catheter tube. In addition, for any everted length of everting catheter 11, the everting pressure within the annular region 14 may be removed and a negative pressure, or vacuum, may be applied to the annular region 14 instead. This vacuum or low pressure is not sufficient to collapse the more rigid conventional catheter 10 but is sufficient to draw the flexible thin-walled everting catheter tube 11 radially outward to an open position. The open everting catheter tube becomes a lumen for infusion and aspiration through the total catheter assembly (assuming that the tail end of the everting tube is appropriately configured).

The prior art techniques for bonding the head end of the everting catheter tube 11 to the primary catheter tube 10 result in serious problems. In the embodiment of FIG. 1, the toposcopic or everting tube 11 is strained considerably during the bonding process, often causing rupture of the everting catheter tube during pressurization of the annular region 14. During clinical use a radiologist often reconfigures the catheter tip by "heat setting" a desired radius or bend in that tip. This "heat set" is also applied to the bond, due to its location at the tip. The heat generated during this process degrades the strength of the bond and the everting tube 11 itself.

In the embodiment illustrated in FIG. 2, the annular pressures required to initiate eversion and to overcome the restriction of a double wall thickness during eversion are very high and, therefore, often lead to failure of the everting catheter element. Moreover, a tearing stress exists on the bond due to the tendency of the bonded wall to evert with the tail of the toposcopic or everting element. In both embodiments the toposcopic element is thermally degraded during the bonding process.

In addition to the problems associated with the bonding techniques employed at the head end in prior art everting catheter assemblies, the tail end configuration of prior art assemblies also has disadvantages. Specifically, the prior art tail configuration generally comprises a complex of tubes, sleeves and mechanical screw fittings which are intended to seal the lumen from the annular region 14 and prevent reverse eversion of the everting element and to provide a rigid metal extension tube for the tail of the everting element. The metal extension was deemed necessary in order to seal the annular space 14.

In order to accommodate these structural elements and their movement, it was necessary to employ a large diameter tube appended to the smaller conventional catheter tube 10 at the proximal end of that catheter tube. This large tube, by necessity, contained an unrestrained length of the tail of the toposcopic element. Lumen infusion pressures required for clinical use of the catheter easily burst the thin-walled toposcopic element where it is unrestrained. that portion of the toposcopic or everting element contained within the conventional catheter is restrained by the catheter.

Another problem associated with prior art everting catheter assemblies relates to filling the narrow annular passage region 14 with sterile media. Specifically, the closed annular space 14 is pressurized to permit the everting catheter 11 to evert. Since the distal or everted-most end of the everting catheter 11 is sealed at the time the region 14 is pressurized, and since complete filling of the region 14 is required for optimal everting and safety in the event of an annular rupture, it is necessary to remove the pre-existing nonsterile fluid from the leading end of the annular region as the pressurized sterile media travels toward that leading end. There is no acceptable apparatus or procedure for accomplishing this in the prior art.

OBJECTS AND SUMMARY OF THE INVENTION

It is therefore an object of the present invention to eliminate mechanical strain and thermal degradation of the everting catheter element at its bond to the primary catheter element.

It is another object of the present invention to reduce the mechanical strain on the bond between the everting and primary catheters during eversion of the everting catheter tube.

It is a further object of the present invention to provide an improved bond between the primary and everting catheter tubes which permits the lowest possible everting pressure to be employed and thereby the safest eversion of the toposcopic catheter.

Still another object of the present invention is to provide an improved bond between the toposcopic and primary catheter elements which permits a radiologist full latitude to "heat set" bends in the catheter tip without jeopardizing bond integrity.

A still further object of the present invention is to provide an improved tail end configuration for an everting catheter assembly which permits increased catheter infusion and aspiration rates while eliminating mechanical fittings so as to assure a viable lumen.

Still another object of the present invention is to provide a tail end configuration for an everting catheter assembly which permits reliable sealing of the infusate while preventing reverse eversion of the toposcopic element.

It is yet another object of the present invention to provide a tail end configuration for a toposcopic catheter assembly which provides for a flexible dynamic sealing mechanism for eversion and retraction of the toposcopic element.

Yet another object of the present invention is to provide a toposcopic catheter assembly having a tail end which permits the toposcopic catheter to adapt its functional complexity to the skill range of the radiologist.

It is also an object of the present invention to provide a simple and efficient means for permitting complete filling of the annular cylindrical region of a toposcopic catheter assembly so as to eliminate bubbles of pre-existing non-sterile fluid.

In accordance with one aspect of the present invention the everting catheter has its open head end turned inside out so that the inner surface of the flexible catheter tube is secured to the interior surface of the outer primary catheter tube with the open head end of the everting catheter facing away from the open distal end of the primary catheter. The length of everting catheter which is bonded to the interior wall of the primary catheter is disposed at a location which is recessed from the distal end of the primary catheter. One technique for effecting this bond employs a hollow mandrel in which the everting catheter is disposed with its open head end folded back onto the outer surface of the mandrel. The mandrel is inserted into the primary catheter tube at the desired location so that the exposed length of the everting catheter tube abuts the interior surface of the primary catheter tube. A bond is effected between the exposed length of the everting catheter tube and the primary catheter, such as by means of heat conducted to the mating surfaces through the catheter wall or deposited locally by radiative (ultrasonic, radiofrequency, infrared, etc.) interaction and heating between the mating surfaces.

This bond permits the lowest eversion pressures to be employed because the bond requires an already partially everted toposcopic catheter tube during the bonding process. Low everting pressures are also permitted because the additional wall thickness required in the prior art embodiment of FIG. 2, which causes a narrowed passageway for the toposcopic element to traverse, is eliminated. Since the everted bond is made by the everted inner surface of the everting catheter tube and the inner circumference of the outer catheter tube, no strain is placed on the element to achieve bonding. The bond is recessed, as described, from the distal end of the outer catheter tube and therefore is well removed from that portion of the catheter which is reconfigured by the radiologist through the application of heat. Moreover, during construction of the bond, thermal bonding energy may be effectively convected away from the internal bond area by a forced flow of cooling fluid through the lumen formed by the toposcopic element.

In accordance with another aspect of the present invention a seal tube of greater rigidity than the everting catheter tube is bias cut and inserted into the open tail end of the everting catheter. The overlapping portions of the everting catheter and the bias-cut seal tube are bonded together to provide a continuous lumen passage through the seal tube and the everting catheter. The bias cut of the seal tube provides for the complete collapse of the toposcopic element upon pressurization of the annular cylindrical region, partially against the protruding and more rigid bias cut area. Since the protruding bias does not preferentially bend so as to evert within itself, a geometrically unbalanced collapse of the toposcopic element occurs. This prevents the toposcopic element from everting away from the catheter tip (i.e., back into the lumen of the seal tube).

In accordance with another aspect of the present invention, pre-existing fluid disposed at the leading or everted-most end of the annular cylindrical space in the everting catheter tube is bled from that space by means of a bleed tube extended longitudinally through the annular cylindrical space to the leading end region. As pressurized sterile fluid is injected into the annular region, air or other fluid which occupies the annulus flows to the leading end of the annulus and into the tip of the bleed tube. The sterile fluid may be supplied by means of a syringe connected to a fitting which is in flow communication with the annular cylindrical region. A seal is provided in the fitting to permit longitudinal withdrawal of the bleed tube without compromising the pressure seal. A valve disposed in the flow path can be closed to trap the sterile fluid within the annular region so that the syringe can be removed without loss of pressurization or introduction of bubbles from the environment.

BRIEF DESCRIPTION OF THE DRAWINGS

These and other objects, features and many of the attendant advantages of the present invention will be better understood from reading the following detailed description considered in connection with the accompanying drawings wherein like parts in each of the several figures are identified by the same reference numerals, and wherein:

FIG. 1 is a view in longitudinal section of an everting catheter tube assembly showing one form of prior art bonding technique between the everting catheter and the containing primary catheter;

FIG. 2 is a view in longitudinal section showing an everting catheter tube assembly using another prior art bonding technique and wherein the assembly is shown in its non-everted state;

FIG. 3 is a view in longitudinal section of the prior art embodiment of FIG. 2 wherein the everting catheter tube is shown partially everted;

FIGS. 4, 5 and 6 illustrate respective successive steps of a bonding technique according to the present invention which results in a bond between an everting catheter tube and its containing primary catheter, the bond itself also constituting part of the present invention;

FIG. 7 is a view in longitudinal section of the bond formed at the head end of an everting catheter tube to join that tube to a containing primary catheter tube in accordance with the present invention;

FIG. 8 is a view in longitudinal section showing a bond formed at the tail end of an everting catheter tube as part of the everting catheter assembly of the present invention; and FIG. 9 is a view in longitudinal section showing a bleed tube structure employed to remove non-sterile pre-existing fluid from the annulus of an everting catheter.

DESCRIPTION OF THE PREFERRED EMBODIMENTS

Referring specifically to FIG. 4 of the accompanying drawings, a bond at the head end of an everting catheter 21, which is to be selectively everted from within a primary catheter 20, is formed by means of a hollow rigid mandrel 27. The mandrel 27 is inserted into primary catheter tube 20 with its leading end 28 extending from the distal end 25 of the primary catheter. The everting catheter 21 is disposed within the mandrel 27 with a length 29 of the everting catheter, including its head end 26, projecting forwardly of the lead end 28 of the mandrel 27. A portion of this projecting length of the everting catheter 21 is folded back onto the exterior surface of mandrel 27 leaving a short everted portion 22 of length 29 projecting forwardly of the mandrel. The relative diameters of the mandrel 27 and the everting catheter tube 21 are such that the folded back portion of length 29 of the everting catheter fits snugly about the exterior surface of mandrel 27 along the axial and circumferential lengths of mutual contact. In addition, the relative diameter of the exposed interior surface of length 29 of the everting catheter, when circumscribing a portion of mandrel 27, is substantially equal to the interior surface diameter for primary catheter tube 20. The mandrel 27 can thereby be withdrawn into the primary catheter tube 20 so that the exposed part of the folded back portion 29 of the everting catheter is in contact with the interior surface of the primary catheter tube 20.

In performing the method of the present invention, the mandrel 27, with a portion of the end length 29 of the toposcopic catheter 21 folded over its forward end 28, is withdrawn into the primary catheter tube 20 so that the forward end 28 is recessed a desired distance from the distal end 25 of the primary catheter tube. In this regard, the stated desired distance is generally at least equal to the axial length of the folded back portion 29 of the toposcopic catheter. With the mandrel thusly positioned, as illustrated in FIG. 6, a bond is then made between the toposcopic element 21 and the primary catheter tube 20. Specifically, the bond is made between the outwardly-facing interior surface of the folded back portion 29 of toposcopic catheter 21 and the adjacent surrounding interior surface portion of primary catheter 20. The materials of the bonded parts are chosen to be appropriate to formation of a strong cohesive bond upon the application of heat (illustrated by the arrows in FIG. 6) to the bonding surfaces. Polyurethanes serve well for this purpose. Heat may be conducted to the mating surfaces through the primary catheter wall, as illustrated in FIG. 6, or may be deposited locally by radiative interaction and heating between the mating surfaces. The short everted portion 22 which extends forwardly of the mandrel is effective to remove the fold location from the heated mandrel tip. If the fold were located on the tip it would tend to heat set and resist eversion during operation. Since the bond strength is determined by a temperature-pressure relationship, an external constrictive pressure applied circumferentially about the primary catheter outer wall, along the bond area, is preferred. An effective means of applying such pressure is the constriction of thermally shrinkable tubing (not shown) placed about the bond area. Upon application of heat from externally of the primary catheter tube, the heat shrinkable tubing shrinks quickly to provide pressure as the bond forms. Typically, Teflon heat shrinkable tubing is preferred to facilitate removal of the shrunken tubing from the catheter surface and to maintain the appearance and properties of the tubing at that surface. Semicylindrically shaped radiative applicator tips may also be effective in applying pressure during radiative bonding.

Mandrel 27 must be rigid enough to withstand the bonding pressures without strain. In addition, mandrel 27 is made of a material which does not thermally bond to the toposcopic element 21. Stainless steel is a preferred material for the mandrel 27. After the bond has been formed the mandrel 27 is twisted, to break adhesive contact, and withdrawn from the opposite end (to the right in FIG. 6) of the primary catheter 20, leaving the everting or toposcopic catheter element bonded to and nested within the primary catheter. The resulting product is illustrated in FIG. 7 wherein partial eversion of the toposcopic element 21 is shown in phantom lines.

The bond and bonding technique described above for the head end of the everting catheter eliminates substantially all of the disadvantages associated with prior art bond and bonding techniques for toposcopic catheter head ends within a primary catheter. The bond can be located at substantially any point within the primary catheter. Moreover, the bond of the present invention permits eversion with the lowest possible pressures because the everting catheter is bonded into a partially everted position during the bonding process. In addition, an additional wall thickness, which creates a narrow passageway for the toposcopic element to traverse in prior art bonds, is eliminated. Since the everted bond is made between the outer circumference of the everted toposcopic element 21 and the inner surface of the primary catheter 20, no strain is placed on the everting element to achieve bonding. The bond is recessed and is therefore well removed from that portion of the catheter which is reconfigured by a radiologist by application of heat prior to use. Moreover, during the bonding method, thermal energy may be effectively convected away from the internal bond area by forced flow of a cooling fluid through the lumen portion 24 of the everting catheter. In this regard cool air is the recommended fluid. Such cooling prevents thermal degradation of the element during the bonding process.

Referring now to FIG. 8 of the accompanying drawings, the sealing technique for the tail end of the toposcopic element is clearly illustrated. Specifically, the toposcopic element 31 has a length 32 at its open tail end which is slipped or slid over a short length at the open end of a seal tube 33. The open end of the seal tube is cut on a bias 34. The toposcopic element 31 is bonded to the seal tube 33 along the length of tail end portion 32 which is in contact with the outer surface of the seal tube 33. The bias cut 34 at the forward end of the seal tube provides for the complete collapse of the toposcopic element 31 (upon pressurization of the toposcopic element annulus during eversion) partially against the protruding and more rigid bias cut area 34.

As the protruding bias 34 does not preferentially bend so as to evert within itself, a geometrically unbalanced collapse of the toposcopic element 31 occurs. This condition prevents the toposcopic element 31 from everting away from the head end of the catheter (that is, back into the interior of the seal tube and the lumen provided thereby).

The seal tube 33 is made of an appropriate material to permit cohesive bonding between itself and the toposcopic element. The bonding may be a chemical or thermal bond, and polyurethanes are the preferred material to provide a bond as strong as the materials themselves. The diameters of the toposcopic element 31 and seal tube 33 are not significantly altered for or by the bonding process. Therefore the bonded length of the seal tube (i.e., the length disposed within portion 32 of the toposcopic element), and the seal tube 33 itself, of diameters substantially less than the interior diameter of the primary catheter 30, move quite freely within the primary catheter 30. The bond is made, however, with a small portion of the tail end of the toposcopic element positioned outside the primary catheter 30 by moderately stretching the toposcopic element 31. Upon the release of an appropriately stretched everting element 31, the bonded length 32 of the seal tube 33 may be made to reside at substantially any longitudinal position within the primary catheter 30. In this way, the everting element 31 may be configured as short as practicable, given a desired ultimate everted length of the everting element 31.

The annular space 35 for receiving pressurized fluid to evert the everting catheter 31 is terminated, at the rear end of the device, by a dynamic seal. The dynamic seal includes a housing 36 secured to the proximal end of the primary catheter 30. Seal tube 33 extends through a bore 37 defined through housing 36 and is spaced from the inner surface of the bore to provide part of the annular pressurization region for everting the toposcopic element 31. The bore 37 extends to the rearward end of housing 36, and the seal tube extends outwardly through the bore so that it can be controlled from externally of the housing. The rearward end of the housing is threaded at 38 to permit threaded engagement with a similarly threaded gland member 39. An annular elastomeric seal member 40 is disposed between the gland member 39 and the rearward end of the housing 36, concentrically about the seal tube 33, so that the seal tube can slide longitudinally through the bore 37 and relative to the seal member 40 while pressure-isolating the bore from the external environment. Seal member 40 thus serves as a dynamic seal for the pressurization fluid used to effect eversion of the toposcopic element 31.

Seal tube 33 is preferably made of relatively high durometer, flexible material, such as polyurethane. In any event, the seal tube 33 is of greater rigidity than the toposcopic element. The seal member 40 and the flexibility of seal tube 33 permits movement of seal tube 33 to control the eversion and retraction of the toposcopic element 31. Seal tube 33 maintains this capability while traversing bends formed in the primary catheter 30 when the latter is placed in a curved bodily passage during clinical procedures. This configuration permits a radiologist, using the catheter, to bend the seal tube 33 at will while still maintaining a compact and sterile assembly.

Housing 36 includes a fitting 41 having an internal passage which communicates with the annular space 35. Pressurized fluid is delivered through passage 42 in fitting 41 to effect eversion of the toposcopic element 31.

The tail end bond and bonding technique described in relation to FIG. 8 overcomes the disadvantages mentioned hereinabove in prior art devices. Specifically, the tail end bond of the present invention permits high infusion/aspiration pressures, and accompanying flow rates, which are required for clinical use by eliminating all unrestrained lengths of the toposcopic element. In this regard, the primary catheter restrains the entire tail of the toposcopic element. In addition, the tail bond of the present invention permits greatly simplified manufacturing techniques to be employed by eliminating complex tail fittings. Further, the tail bond of the present invention provides a reliable seal between the lumen and annulus at the tail of the toposcopic element to prevent lumen-to-annulus leakage. The tail end bond of the present invention includes a simple and easily manufactured bias cut 34 to prevent reverse eversion of the toposcopic element. Finally, the tail end bond of the present invention provides a small flexible sealing mechanism which eliminates the unwieldy rigid metal extension tube commonly used.

In accordance with another aspect of the present invention, and referring to FIG. 9, a technique if provided for permitting pre-existing fluid to escape from the pressurized annulus in the everting catheter when sterile media is applied to effect eversion. In order to fill the very narrow passage which the annulus forms, media must be transported to the very tip 43 of the closed annulus in the toposcopic element 31. Since the annulus is a closed space, the contents of the annulus must be allowed to escape as the entering media displaces it. For this purpose, the fitting 41 is provided with a three-way stop cock 44 disposed in passage 42. One end of the stop cock 44 is exposed to the everting pressurization annulus 35 via passage 42. The opposite end of the stop cock 44 is exposed to the bleed tube seal fitting 46, which end serves as a continuation of passage 42 when the stop cock 44 is turned to the appropriate position. A sterile syringe 45 is connected to the third port of the stop cock 44 for purposes of injecting sterile pressurization media into the annular space 35. A bleed tube 47 extends from outside the bleed tube seal fitting 46 attached to fitting 44, through a dynamic seal 48 and passage 42 into the annular space 35 of the everting catheter 31. The tip 49 of bleed tube 47 extends all the way to the forward end of the annular space 35, or substantially to the forward tip 43 of the everting catheter 31. As media is injected into the annular space 35 from syringe 45, air or other fluid which previously occupied the annular space is forced to flow into the tip 49 of the bleed tube and out through that tube to ambient environment or other low pressure region. In this regard, it is noted that the bleed tube 47 serves as the only port for venting or bleeding the annular region 35. Once the annular region 35 is continuously pressurized by the syringe, the seal 40 at the rearward end of fitting 41 may be loosened slightly to permit any air trapped at the seal to escape and retightened. Thus, a gland member my be loosened to loosen the seal accordingly. With pressure from the syringe maintained, the bleed tube 47 is withdrawn through the seal 48 until it is removed from the fitting 46. In this regard, the seal 48 is shown schematically in FIG. 9 but is preferably of the same type illustrated in FIG. 8 for seal 40. Stop cock 44 is then adjusted to close the annular space 35 and syringe 45 is then removed. The catheter assembly may then be presented to the remainder of the system for clinical use with the annular space 35 completely filled with sterile media. Stop cock 44 is then finally adjusted to provide communication between the catheter annulus and the balance of that system.

It should be noted that the injected sterile media may also be supplied from the balance of the annular system rather than from a separate syringe 45. In any case, the bleed tube 47 forms the mechanism for escape of displaced air in the annulus and allows a completely filled and bubble-free annulus.

I have described herein an improved everting catheter assembly, and method of fabricating such assembly, which has numerous advantages over prior art apparatus and methods. In one aspect of the invention an everting or toposcopic catheter is disposed within a primary such that the open head end of the everting catheter faces away from the distal end of the primary catheter and is secured to the interior wall of the primary catheter. In another aspect of the invention the everting catheter is secured within the primary catheter at a location which is considerably spaced from the distal end of the primary catheter. The tail end of the everting catheter is bonded to a flexible but more rigid seal tube having a bias cut end disposed within the tail end of the everting catheter. A dynamic seal permits control of the longitudinal position of the seal tube within the annular everting catheter space without loss of pressurization. Finally, pre-existing fluid in the annular space is removed upon pressurization of that annular space with sterile media by means of a bleed tube extending through the annular space from the forward end thereof.

While I have described and illustrated specific embodiments of my invention, it will be clear that variations of the details of construction which are specifically illustrated and described may be resorted to without departing from the true spirit and scope of the invention as defined in the appended claims.

I claim:

1. A catheter assembly comprising:
  a primary catheter in the form of an elongated hollow tube having an interior wall and an open distal end;
  an everting catheter disposed within said primary catheter and having an open head end facing away from said distal end of said primary catheter and secured to the interior wall of said primary catheter; and
  means for selectively everting said everting catheter along said interior wall in a direction toward and out through the open distal end of said primary catheter;
  wherein said open head end of said everting catheter is secured to said interior wall along a predetermined length of said interior wall which is recessed from said distal end of said primary catheter.

2. The catheter assembly according to claim 1 wherein said predetermined length of said interior wall is spaced from said distal end of said primary catheter by a distance which is at least equal to said predetermined length.

3. The catheter assembly according to claim 1 wherein said everting catheter is a thin walled flexible and collapsible tube having inner and outer surfaces, wherein said head end of said everting catheter is secured to the interior wall of said primary catheter along a predetermined length of said inner surface of said collapsible tube, wherein said outer surface of said collapsible tube defines a generally annular cylindrical space with said interior wall of said primary catheter, and wherein said means for selectively everting includes means for pressurizing said annular cylindrical space to evert at least a portion of said everting catheter along said interior wall and out through said distal end of said primary catheter with the inner surface of the everted portion of said collapsible tube facing outward.

4. The catheter assembly according to claim 3 wherein said everting catheter has an open tail end longitudinally opposite said open head end, said assembly further including a seal tube of greater durometer than said everting catheter and having a bias-cut end secured within said everting catheter at said open tail end.

5. The catheter assembly according to claim 4 further comprising a housing, wherein said primary catheter includes a proximal end secured to and opening into said housing, wherein said housing includes an interior region in flow communication with said annular space and an access opening through which said seal tube extends into said interior region and said primary catheter, and further including dynamic seal means surrounding said seal tube proximate said access opening to permit longitudinal movement of said seal tube through said access opening while providing a pressure seal about said seal tube at said access opening, said dynamic seal means comprising an annular elastomeric member disposed about said seal tube.

6. The catheter assembly according to claim 5 wherein said dynamic seal means further comprises a threaded gland member threadedly engaging said housing about said access opening and having a through hole defined therein in longitudinal alignment with said access opening, said annular elastomeric member being disposed between said gland member and said housing so as to be selectively compressed between the gland member, the housing and the seal tube as the threaded engagement between the gland member and housing is tightened.

7. The catheter assembly to claim 6 wherein said means for selectively everting includes port means in said housing for supplying pressurized fluid to said housing interior region and to said annular cylindrical space.

8. The catheter assembly according to claim 7 further comprising bleed means responsive to application of pressurized fluid to said annular cylindrical space for bleeding pre-existing fluid from that space, said bleed means comprising a bleed tube having an open forward end disposed in said annular cylindrical space proximate the everted-most end of said collapsible tube, and an opposite end disposed in a relatively low pressure environment exteriorly of said housing.

9. The catheter assembly according to claim 8 wherein said bleed tube is selectively removable from said annular cylindrical space, wherein said housing has a bleed tube opening defined therein through which said bleed tube extends, said assembly further comprising bleed tube seal means for pressure sealing said bleed tube opening against said bleed tube while permitting longitudinal movement of said bleed tube through said bleed tube opening.

10. The catheter assembly according to claim 9 wherein said means for supplying pressurized fluid includes fitting means secured to said housing for conducting pressurized fluid into said housing interior region, syringe means removably secured to said housing for injecting pressurized fluid through said fitting means and into said housing interior region, and selectively actuable valve means for alternatively opening and blocking flow to said fitting means from said syringe means.

11. The catheter assembly according to claim 10 wherein said fitting means includes a flow passage formed integrally with said housing and oriented to conduct pressurized fluid to said housing interior region, and wherein said bleed tube extends through said flow passage to said bleed tube opening.

12. The catheter assembly according to claim 3 further comprising bleed means responsive to application of pressurized fluid to said annular cylindrical space for bleeding pre-existing fluid from the space, said bleed means comprising a bleed tube movable in said annular cylindrical space independently of said primary catheter and having an open forward end disposed in said annular cylindrical space proximate the everted-most end of said collapsible tube, and an opposite end disposed in a relatively low pressure environment.

13. The catheter assembly according to claim 12 further comprising a housing, said proximal end of said primary catheter being secured to and opening into said housing, wherein said bleed tube is selectively removable from said annular cylindrical space, wherein said housing has a bleed tube opening defined therein through which said bleed tube extends, said assembly further comprising bleed tube seal means for pressuresealing said bleed tube opening against said bleed tube while permitting longitudinal movement of said bleed tube through said bleed tube opening.

14. A catheter assembly comprising:
a primary catheter in the form of an elongated hollow tube having an interior wall and an open distal end;
an everting catheter disposed within said primary catheter and having an open head end, said everting catheter comprising a thin-walled flexible and collapsible tube having inner and outer surfaces, wherein said open head end of said everting catheter is secured to the interior wall of said primary catheter along a predetermined length of said inner surface of said collapsible tube defines a generally annular cylindrical space between itself and the interior wall of said primary catheter; and
means for selectively everting said everting catheter including means for pressurizing said annular cylindrical space to evert at least a portion of said everting catheter along said interior wall and out through said distal end of said primary catheter with the inner surface of the everted portion of said collapsible tube facing outward;
wherein said everting catheter has an open tail end longitudinally opposite said open head end, said assembly further including a seal tube of greater rigidity than said everting catheter and having a bias-cut end bonded to and within said everting catheter at said open tail end.

15. A catheter assembly comprising:
a primary catheter in the form of an elongated hollow tube having an interior wall and an open distal end;
an everting catheter disposed within said primary catheter and having an open head end, said everting catheter comprising a thin-walled flexible and collapsible tube having inner and outer surfaces, wherein said open head end of said everting catheter is secured to the interior wall of said primary catheter along a predetermined length of said inner surface of said collapsible tube, wherein said outer surface of said collapsible tube defines a generally annular cylindrical space between itself and the interior wall of said primary catheter;
means for selectively everting said everting catheter including means for pressurizing said annular cylindrical space to evert at least a portion of said everting catheter along said interior wall and out through said distal end of said primary catheter with the inner surface of the everted portion of said collapsible tube facing outward;
a housing, wherein said proximal end of said primary catheter is secured to and opens into said housing; and
bleed means responsive to supplying pressurized fluid to said annular cylindrical space for bleeding pre-existing fluid from that space, said bleed means comprising a bleed tube movable in said annular space independently of said primary catheter and having an open forward end disposed in said annular cylindrical space proximate the everted-most end of said collapsible tube, and an opposite end disposed in a relatively low pressure environment exteriorly of said housing.

16. The catheter assembly according to claim 15 wherein said bleed tube is selectively removable from said annular cylindrical space, wherein said housing has a bleed tube opening defined therein through which said bleed tube extends, said assembly further comprising bleed tube seal means for pressure-sealing said bleed tube opening against said bleed tube while permitting longitudinal movement of said bleed tube through said bleed tube opening.

17. The catheter assembly according to claim 14 further comprising a housing, wherein said primary catheter includes a proximal end secured to and opening into said housing, wherein said housing includes an interior housing region in flow communication with said annular space and an access opening through which said seal tube extends into said interior region and into said primary catheter, and further including dynamic seal means surrounding said seal tube proximate said access opening to permit longitudinal movement of said seal tube through said access opening while providing a pressure seal about said seal tube at said access opening, said dynamic seal means comprising an annular elastomeric member disposed about said seal tube.

18. A catheter assembly comprising:
a primary catheter in the form of an elongated hollow tube having an interior wall and an open distal end;
an everting catheter disposed within said primary catheter and having an open head end, said everting catheter comprising a thin-walled flexible and collapsible tube having inner and outer surfaces, wherein said open head end of said everting catheter is secured to the interior wall of said primary catheter along a predetermined length of said inner surface of said collapsible tube, wherein said outer surface of said collapsible tube defines a generally cylindrical space between itself and the interior wall of said primary catheter; and
means for selectively everting said everting catheter including means for pressurizing said annular cylindrical space to evert at least a portion of said everting catheter along said interior wall and out through said distal end of said primary catheter with the inner surface of the everted portion of said collapsible tube facing outward;
wherein said open head end of said everting catheter is secured to said interior wall of said primary catheter along a predetermined length of said interior wall, said predetermined length of said interior wall being recessed from said distal end of said primary catheter by a distance which is at least equal to said predetermined length.

19. A catheter assembly comprising:
a primary catheter in the form of an elongated tube having an interior wall and an open distal end;
an everting catheter having a head end secured to said interior wall, said everting catheter being disposed within said primary catheter;
means for selectively everting said everting catheter from within said primary catheter and out through the distal end of said primary catheter;
wherein said everting catheter has an open tail end longitudinally opposite said open head end, said assembly further including a seal tube of greater rigidity than said everting catheter and having a bias-cut end bonded within said everting catheter at said open tail end.

20. The catheter assembly according to claim 19 further comprising:
a housing, said proximal end of said primary catheter being secured to and opening into said housing;
wherein said everting catheter is a thin-walled flexible and collapsible tube having inner and outer surfaces;
wherein said outer surface of said collapsible tube defines a generally annular cylindrical space within said interior wall of said primary catheter; and
bleed means responsive to application of pressurized fluid to said annular cylindrical space for bleeding pre-existing fluid from that space, said bleed means comprising a bleed tube having an open forward end disposed in said annular cylindrical space proximate the evertedmost end of said collapsible tube, and an opposite end disposed in a relatively low pressure environment exteriorly of said housing.

21. The catheter assembly according to claim 20 wherein said bleed tube is selectively removable from said annular cylindrical space, wherein said housing has a bleed tube opening defined therein through which said bleed tube extends, said assembly further comprising bleed tube seal means for pressure sealing said bleed tube opening against said bleed tube while permitting longitudinal movement of said bleed tube through said bleed tube opening.

22. The catheter assembly according to claim 20 wherein said open head end of said everting catheter is secured to the interior wall of said primary catheter along a predetermined length of said interior surface of said collapsible tube, and wherein said means for selectively everting includes means for pressurizing said annular cylindrical space to evert at least a portion of said everting catheter along said interior wall and out through said distal end of said primary catheter with the inner surface of the everted portion of said collapsible tube facing outward.

23. The catheter assembly according to claim 19 wherein said head end of said everting catheter is open and is secured to the interior wall of said primary catheter tube in an orientation where the open head end faces away from said distal end of said primary catheter.

24. A catheter assembly comprising:
a primary catheter in the form of an elongated tube having an interior wall and an open distal end;
an everting catheter having a head end secured to said interior wall, said everting catheter being disposed within said primary catheter;
means for selectively everting said everting catheter from within said primary catheter and out through the distal end of said primary catheter;
a housing, wherein the primary catheter has a proximal end, opposite said distal end, which is secured to and opens into said housing;
wherein said everting catheter is a thin-walled flexible and collapsible tube having inner and outer surfaces;
wherein said outer surface of said collapsible tube defines a generally annular cylindrical space with said interior wall of said primary catheter; and
bleed means responsive to the application of pressurized fluid to said annular cylindrical space for bleeding pre-existing fluid from that space, said bleed means comprising a bleed tube movable in said annular cylindrical space independently of said primary catheter and having an open forward end disposed in said annular cylindrical space proximate the everted-most end of said collapsible tube, and an opposite end disposed in a relatively low pressure environment exteriorly of said housing.

25. The catheter assembly according to claim 24 wherein said head end of said everting catheter is open and secured to the interior wall of said primary catheter along a predetermined length of said interior surface of said collapsible tube; and
wherein said means for selectively everting includes means for pressurizing said annular cylindrical space to evert at least a portion of said everting catheter along said interior wall and out through said distal end of said primary catheter with the inner surface of the everted portion of said collapsible tube facing outward.

26. The catheter assembly according to claim 24 wherein said head end of said everting catheter is open and is secured to the interior wall of said primary catheter tube in an orientation where the open head end faces away from said distal end of said primary catheter.

27. The catheter assembly according to claim 24 wherein said bleed tube is selectively removable from said annular cylindrical space, wherein said housing has a bleed tube opening defined therein through which said bleed tube extends, said assembly further comprising bleed tube seal means for pressure sealing said bleed tube opening against the bleed tube while permitting longitudinal movement of said bleed tube within said bleed tube opening.

28. The catheter assembly according to claim 27 wherein said means for supplying pressurized fluid includes fitting means secured to said housing for conducting pressurized fluid into said housing interior region, syringe means removably secured to said housing for injecting pressurized fluid through said fitting means and into said housing interior region, and selectively actuable valve means for selectively opening and blocking flow to said fitting means from said syringe means.

29. The catheter assembly according to claim 28 wherein said fitting means includes a flow passage formed integrally with said housing and oriented to conduct pressurized fluid to said housing interior region, and wherein said bleed tube extends through said flow passage to said bleed tube opening.

30. A catheter assembly comprising:
a primary catheter in the form of an elongated tube having an interior wall and an open distal end;
an everting catheter having a head end secured to said interior wall, said everting catheter being disposed within said primary catheter;
means for selectively everting said everting catheter from within said primary catheter and out through the distal end of said primary catheter;
a housing, wherein the primary catheter has a proximal end, opposite said distal end, which is secured to and opens into said housing;
wherein said everting catheter is a thin-walled flexible and collapsible tube having inner and outer surfaces;
wherein said outer surface of said collapsible tube defines a generally annular cylindrical space with said interior wall of said primary catheter; and
bleed means responsive to the application of pressurized fluid to said annulay cylindrical space for bleeding pre-existing fluid from that space, said bleed means comprising a bleed tube having an open forward end disposed in said annular cylindrical space proximate the everted-most end of said collapsible tube, and an opposite end disposed in a relatively low pressure environment exteriorly of said housing;
wherein said everting catheter has an open tail end longitudinally opposite said open head end, said assembly further including a seal tube of greater rigidity than said everting catheter and having a bias cut end disposed within and bonded to the everting catheter at said open tail end.

31. The method of securing a thin-walled flexible and collapsible everting catheter tube to the interior wall of a primary catheter tube having a distal end, said method comprising the steps of:
inserting the everting catheter tube into a hollow mandrel tube with a short length at the head end of the everting catheter tube turned inside out and folded back onto the outside surface of the mandrel;
positioning the mandrel and the inserted everting catheter tube within the primary catheter tube such that the head end of the everting catheter tube faces away from the distal end of the primary catheter tube;
wherein the outside diameter of the mandrel tube combined with the thickness of the folded-over short length of the everting catheter tube places the short length of the everting catheter tube in contact with the interior wall of the primary catheter; and
bonding the short length of the everting catheter tube to the interior wall of the primary catheter tube.

32. The method according to claim 31 wherein the step of positioning includes positioning said short length of the everting catheter in spaced relation with respect to the distal end of the primary catheter tube.

33. The method according to claim 32 further comprising the steps of:
stretching the tail end of said everting catheter, located opposite said head end, to overlap beyond a bias cut at the end of a seal tube of suitable size to be inserted longitudinally into said primary catheter and of sufficient rigidity to be longitudinally displaced in said primary catheter from outside said primary catheter; and
bonding the overlapping lengths of the everting catheter and seal tube together.

34. The method of securing the tail end of an everting catheter in a catheter assembly comprising the steps of:
inserting the tail end of an everting catheter to overlap beyond a bias cut at the end of a seal tube of suitable size to be inserted longitudinally into a primary catheter from which the everting is to be everted and of sufficient rigidity to be longitudinally displaced in said primary catheter from outside said primary catheter; and
bonding the overlapping lengths of the everting catheter and seal tube together.

* * * * *